United States Patent [19]

Fay et al.

[11] Patent Number: 5,387,245
[45] Date of Patent: Feb. 7, 1995

[54] INFLATABLE PROSTHESIS LINER

[76] Inventors: John N. Fay; Cheryl A. Fay, both of 1120 Boca Ciega Isle, St. Petersburg, Fla. 33706

[21] Appl. No.: 40,237

[22] Filed: Mar. 30, 1993

Related U.S. Application Data

[63] Continuation-in-part of Ser. No. 814,969, Dec. 23, 1991, abandoned.

[51] Int. Cl.⁶ .............................. A61F 2/80; A61F 2/76
[52] U.S. Cl. ........................................ 623/37; 623/34; 623/901
[58] Field of Search .................... 623/33–37, 623/901; 264/222, DIG. 30; 156/275.3, 308.4

[56] References Cited

U.S. PATENT DOCUMENTS

| | | | |
|---|---|---|---|
| 4,300,245 | 11/1981 | Saunders | 623/37 X |
| 4,923,475 | 5/1990 | Gosthnian et al. | 623/37 |
| 5,246,464 | 9/1993 | Sabolich | 623/33 |

FOREIGN PATENT DOCUMENTS

| | | | |
|---|---|---|---|
| 2420335 | 10/1979 | France | 623/37 |
| 2353565 | 5/1974 | Germany | 156/308.4 |

Primary Examiner—David H. Willse
Attorney, Agent, or Firm—Joseph C. Mason, Jr.; Ronald E. Smith

[57] ABSTRACT

A liner that covers an amputation stump and which cushions the stump when it is placed into a prosthesis socket includes selectively inflatable bladders foe customizing the liner to fit individual patients. The liner is made of two liner parts, one being an inner liner and the other being an outer liner. The inner liner is placed onto the amputation stump and a prosthetist determines the region or regions where bladders are needed to provide a comfortable fit. The region or regions are outlined with an adhesive and the outer liner is then brought into overlying relation to the inner liner so that the two liner parts adhere to one another along the outlined regions. Upon inflation, the inner liner conforms to the shape of the amputation stump to provide enhanced cushioning and the outer liner conforms to the shape of the interior wall of the socket and the patient receives a custom fit from a simple appliance. An annular bladder at the proximal rim of the socket creates a substantially perfect seal to maintain the suction within the socket.

4 Claims, 4 Drawing Sheets

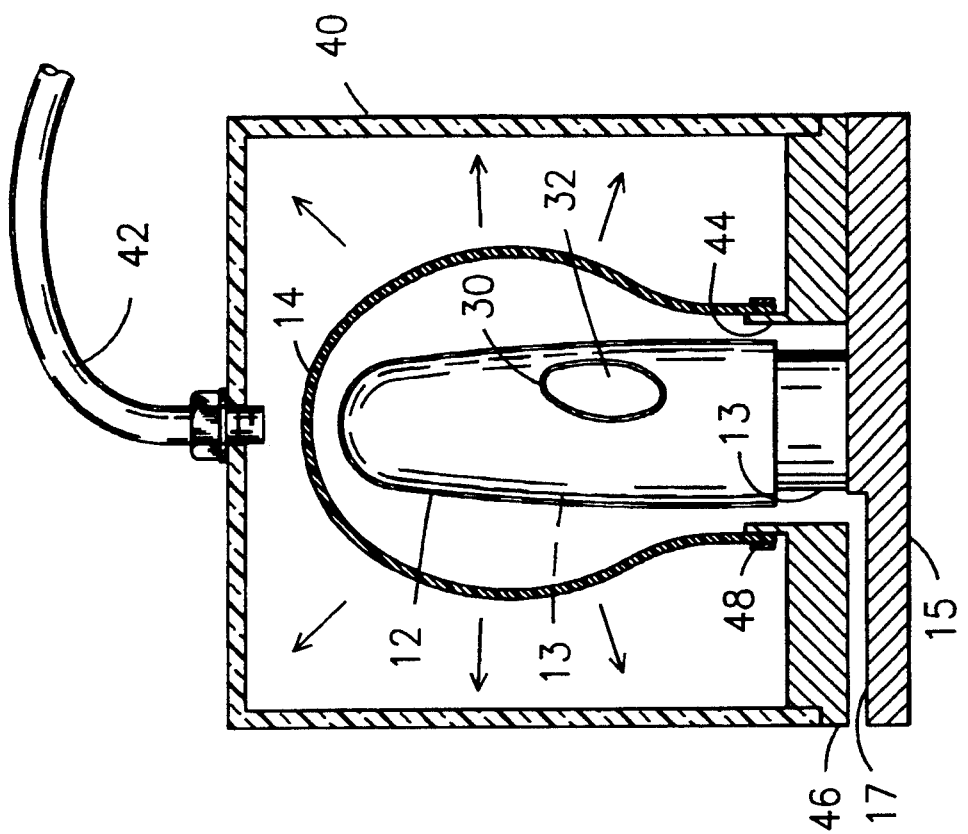
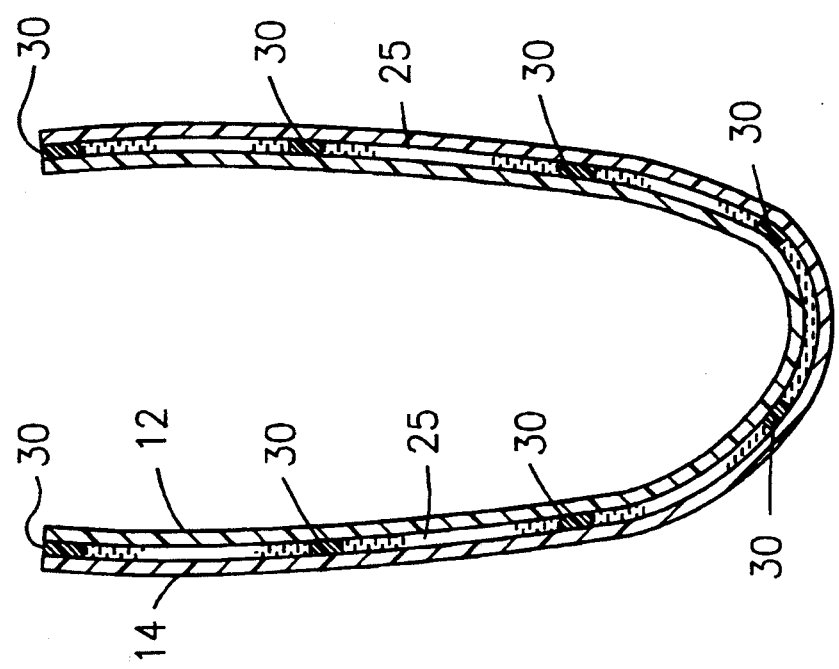

INFLATABLE PROSTHESIS LINER

This is a continuation-in-part of copending application Ser. No. 07/814,969 filed on Dec. 23, 1991, now abandoned.

TECHNICAL FIELD

This invention relates, generally, to prostheses. More particularly, it relates to a liner that cushions an amputation stump received within a hard socket.

BACKGROUND ART

The crudest form of a prosthesis is a hard, stump-receiving socket. If a socket is for receiving the stump of a below-the-knee amputee, it will be attached by suitable means to a prosthetic foot; if it is for an above-the-knee amputee, it will be attached to a prosthetic knee as well. In either application, the amputee will experience discomfort arising from contact between the stump and the hard interior of the stump,receiving socket unless an adequate cushioning means is provided.

Some prosthetic devices are held onto the residual limb (amputation stump) by suction. A one way valve releases air from the socket as the residual limb is inserted thereinto. When the residual limb is fully inserted, the tissue is pulled slightly downwardly and this creates a suction within the socket that holds it on. Obviously, this suction must be maintained if the socket is to remain in place.

Some individuals fit socks over their residual limb in an attempt to make the prosthesis more comfortable. Several layers of socks will form a reasonably soft cushion, but there are a number of drawbacks to the use of socks as socket liners. Perhaps the most obvious limitation is the inability of socks to protect a particular point or area where extra cushioning is needed, i.e., socks provide the same amount of cushioning everywhere. Moreover, the diameter of a stump will vary during the day, especially where the amputee is active. Specifically, most stumps shrink in size as the day progresses because walking and other activities literally drives blood and other fluids out of the stump; this results in the need for more layers of socks and that need requires the amputee to travel throughout the day with a supply of extra socks on hand. It is also troublesome and time-consuming to remove the socket, add a layer or two of socks, and to reattach the socket several times per day. Amputees who use socks as cushioning means are of course familiar with other drawbacks not mentioned herein.

Perhaps even more problematic than daily stump volume variations are the long term variations brought about by long term weight loss or weight gain.

In response to the limitations of socks as a means for cushioning, inventors have developed a number of alternatives thereto. Perhaps the simplest, most obvious alternative is to line the socket with a cushioning means. The problem with cushioned stump-receiving sockets is equally obvious, i.e., the fit between the socket and the stump becomes loose as the day progresses, and the amputee must again resort to the expedient of employing multiple layers of socks to maintain a reasonably tight fit as required.

Cushioned sockets, like socks, also fail to provide extra cushioning to particular points or areas.

Accordingly, customized cushioning means have been developed so that each individual amputee may have a cushioning means that matches the contour of his or her residual limb. A cast is made of the stump by wrapping plaster bandages around it, or by simply inserting the stump into a vat of impressionable material. The negative of the stump thereby created is then filled with plaster or other suitable material; this produces a replica of the residual limb. A liner is then fabricated that provides the proper amount of cushioning at the places where extra cushioning is needed.

Although liners so fabricated are superior in performance to socks and non-customized liners, they do not compensate for the changes in size of the stump during a day or from day to day. Moreover, such liners are expensive because they must be made for one patient at a time.

In an attempt to provide customized liners that compensate for changes in stump size, inventors have developed liners that include inflatable bladders. Thus, as the day progresses, more air is introduced into preselected bladders to maintain the tight fit between the socket and stump and to maintain the amputee's comfort level.

Even these advanced liners have shortcomings. Their primary drawback is that they must be customized with a high degree of precision for each patient. Thus, they cannot be mass produced and their unit cost is therefore quite high. In U.S. Pat. No. 4,923,475 to Gosthnian et. al., the stump-engaging surface of each bladder is molded to have a shape conforming to the outer surface of the amputee's stump when the stump is under static pressure, i.e., the patient stands to place static pressure on the stump, and the bladders are made so that they conform, when inflated, to the particular contour of the stump thereby produced. This highly exacting procedure does not lend itself to mass production.

U.S. Pat. No. 4,923,474 to Klasson et. al. discloses a liner that has a distal end that is highly elastic in a radial direction so that it tightly and snugly engages the stump as the stump changes size, yet which is substantially inelastic axially so that it is easy to position. No bladders are provided, Thus, to those of ordinary skill in this art, it would appear that liners employing bladders and bladder-free liners have reached a state of such advanced development that the only advances that will be made in the future will relate to better materials, better production techniques, and the like. Nothing whatsoever in the art suggests that liners having inflatable bladders could be mass produced yet precisely fit to individual patients.

DISCLOSURE OF INVENTION

The present invention pioneers the art of mass-produced, low unit cost prosthetic liners having bladders that are customized to the individual user. The novel liners provide a facile means for compensating for daily and long term fluctuations in stump volume.

The novel liner obviates the need to make a negative of the patient's amputation stump, yet produces a liner having bladders that precisely conform to the stump and to the interior surfaces of the stump-receiving socket. Each bladder may be provided with a pump so that its degree of inflation may be adjusted as needed.

The insight behind this breakthrough invention is the discovery that bladders can be formed by placing two non-customized liners of equal size in nested relation to one another. Each liner is mass producable because it is generated simply by rotating a parabola about its axis of symmetry. Individual bladders are formed between the liners by applying a suitable adhesive to the interior liner, outlining the area where the bladder will be. The interior liner is then inserted into the outer liner and the adhesive joins the two liners along the extent of said adhesive, thereby forming a pocket or bladder. In this manner, the inner and outer liners can be manufactured in large quantities to reduce their unit cost, yet each individual user can have the liner customized by his or her physician. More particularly, the physician observes the stump when the interior liner is placed thereon, and marks the areas where bladders are needed. The adhesive is then applied to the inner liner and the outer liner is placed thereover. Alternatively, the physician could apply the adhesive where needed, skipping the marking step.

Air is introduced into or released from each individual bladder by conventional valve means.

An annular bladder may be provided at the uppermost end thereof to form an airtight seal with the proximal end of the socket.

Thus, the novel liner assembly includes:
a flexible inner liner made of an elastomeric material and having a predetermined thickness;
a flexible outer liner made of an elastomeric material and having a predetermined thickness;
said inner liner and said outer liner each having an open proximal end and a rounded, closed distal end;
said inner liner and said outer liner each defining an open-ended cavity;
said inner and outer liners having a common size and shape;
said common shape being generated by rotating a parabola about its longitudinal axis of symmetry;
said inner liner being nested within said outer liner and said outer liner being disposed in overlying, contacting relation to an outer surface of said inner liner throughout the entire surface area of said inner liner;
said inner and outer liners being substantially unconnected to one another;
adhesive means disposed between said inner and outer liners along a predetermined path of travel that forms a closed loop for adhering said liners together along said predetermined path of travel;
at least one bladder area circumscribed by said adhesive means so that at least one bladder is formed within said circumscribed area when said adhesive means dries;
said adhesive means having a narrow width with respect to its length so that said inner and outer liners are unbonded to one another except along the narrow extent of said adhesive means;
said at least one bladder being defined between said inner and outer liners, and being bounded by said adhesive means;
a valve means disposed in fluid communication with said at least one bladder so that air under positive pressure may be admitted thereinto and released therefrom; and
said inner and outer liners being in contact with one another except in the circumscribed area when air is introduced into said at least one bladder;
whereby said inner and outer liners are brought into conformity with the outer surface of a patient's amputation stump and an inner surface of said socket, respectively, upon inflation of said at least one bladder; and
whereby said liners need not be custom made to fit individual patients.

The primary object of this invention is to substantially reduce the cost of prosthetic liners while simultaneously providing an advanced liner that is easily customized to fit individual users with a high degree of comfort.

A closely related object is to provide such a liner having inflatable bladders to accommodate short and long term changes in stump size without loss of suction.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 6 is a sectional view showing how lubricant positioned between the inner and outer liners reduces friction on the patient's skin;

FIG. 8 is a sectional view showing the parts of FIG. 7 in their assembled configuration and showing an additional part.

BEST MODES FOR CARRYING OUT THE INVENTION

Figure 1:
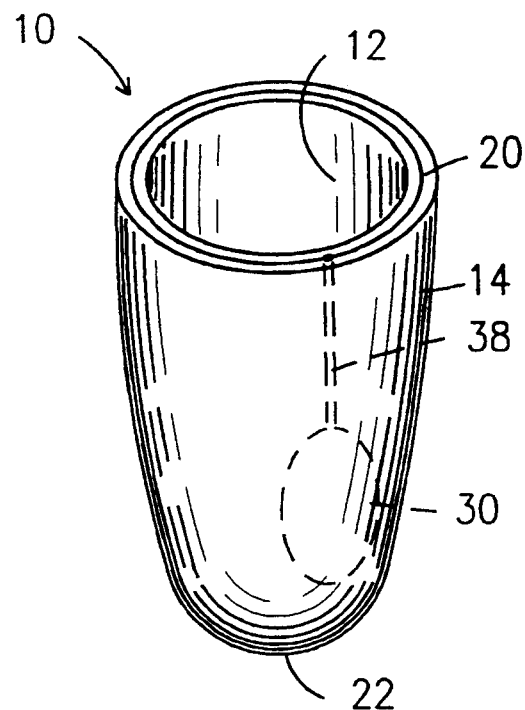
FIG. 1 is a perspective view of an assembled liner, showing a passageway for air to a bladder.

Referring now to FIG. 1, it will there be seen that an exemplary embodiment of the invention is denoted as a whole by the reference numeral 10.

Liner 10 has an inner part 12 and an outer part 14, both of which are formed of the same flexible, elastomeric material. The preferred material is silicone having a high degree of elasticity. Empirical tests have shown that a silicone compound having an elasticity of about twelve hundred per cent is an ideal material.

Inner liner 12 has a proximal open end 16 and a closed distal end 18 (FIG. 2); the diameter of the open end is greater than the diameter of the closed end so that the liner has a generally frustoconical appearance when viewed in side elevation. Similarly, outer liner 14 has a proximal open end 20 and a closed distal end 22, and the former end has a greater diameter than the latter. The two liners have the same size; the outer liner is simply rolled onto the inner liner and the uppermost edge of the inner liner is trimmed off for aesthetic purposes. Where no bladders are to be formed, the inner liner may simply be inserted into the outer.

Each liner has a shape achieved by rotating a parabola about its longitudinal axis of symmetry.

To prepare the liner for use by the patient, inner liner 12 is first placed in overlying relation to the amputation stump by first rolling it inside out and then unrolling it onto the stump, or by any other suitable technique. The physician or prosthetist then observes the liner and residual limb carefully, and notes where bladders will be needed. Those areas where a bladder will be needed, in the professional opinion of the fitter, are circled with a pen or other suitable marker. A silicone, adhesive 30 (FIG. 3), preferably made of the same material as the inner and outer liners, is then applied along the marked lines, and the second or outer liner 14 is placed into overlying relation to the inner liner 12. This may be accomplished in the same manner as used to fit the inner liner over the stump, i.e., the second liner is simply rolled up, inside out, and then unrolled onto the inner liner; this unrolling action is depicted in FIG. 3. In that figure, the unrolled part of outer liner 14 is denoted 15; it is being unrolled in the direction indicated by directional arrow 17. Adhesive 30 may smear to some extent, but not to an appreciable extent. The circumscribed area 32 or areas are separated or demarcated from the areas 34 (FIG. 3) not circumscribed when the adhesive dries, as perhaps best depicted in FIG. 2; such circumscribed areas become the bladders when a pump means is employed to introduce air thereinto, as perhaps best depicted in FIGS. 1 and 4.

Note that the adhesive means extends along a predetermined path of travel that forms a closed loop, and that the width of the adhesive is narrow with respect to its length.

Figure 4:
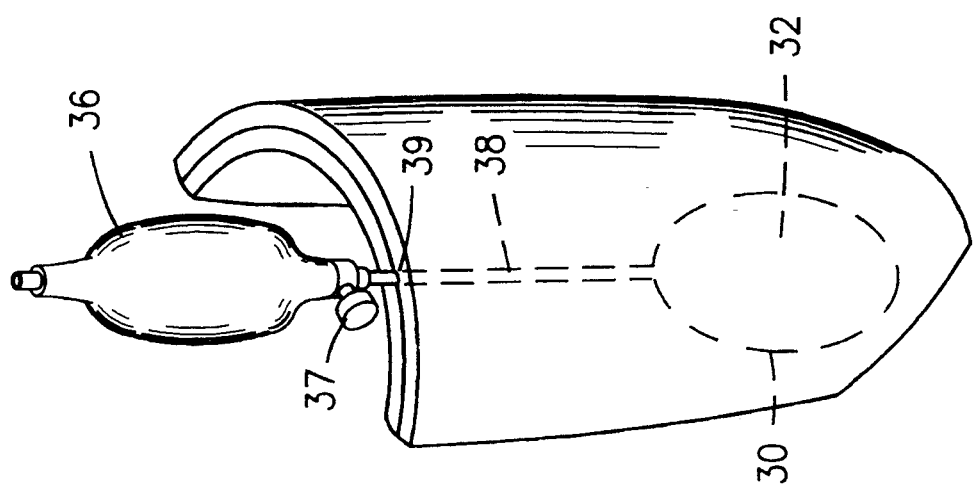
FIG. 4 is a perspective view of an assembled liner, in broken away form, showing a pump means for introducing and removing air into and from the bladder, respectively.

A suitable pump means is denoted 36 in FIG. 4; it includes a bulbous, flexible main body and a valve means 37. Passageway 38 interconnects bladder 32 and said pump 36. A check valve at the uppermost end of passageway 38 prevents flow of air out of bladder 38 when pump 36 is disconnected therefrom; stem 39 of pump 36 opens the check valve when the pump is in use as depicted in FIG. 4.

Figure 5:
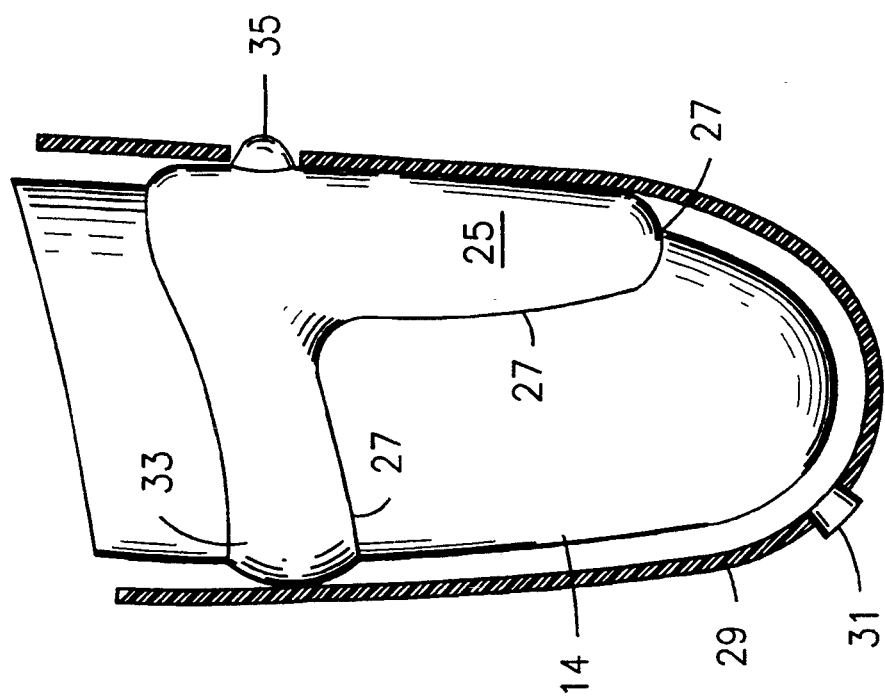
FIG. 5 is a side elevational view showing an embodiment having an annular bladder near the uppermost end of the liner and an integral bladder that depends therefrom.

It is also possible to place the air valve directly into the bladder, thereby eliminating any need for a passageway; such a valve is shown in FIG. 5. Valve 35 is in open fluid communication with annular bladder 33; said annular bladder provides a seal that prevents loss of the vacuum achieved when air in socket 29 escapes, therefrom through check valve 31 when the residual limb is inserted into said socket 29. Reference numeral 27 indicates the elongate seal established between the inflated annular bladder 33 and bladder 25 which is integral therewith and which depends therefrom, and the inner surface of socket 29. The extent of the seal greatly enhances the ability of the novel construction to maintain the vacuum therewithin. The space between outer liner 14 and socket 29 is greatly exaggerated in FIG. 5 to better depict the bladder.

Areas that are not inflated, i.e., areas outside the adhesive borders, are injected with a liquid or dry lubricant 25 (FIG. 6) which allows each liner to slide with respect to the other; this reduces friction to the skin.

Figure 7:
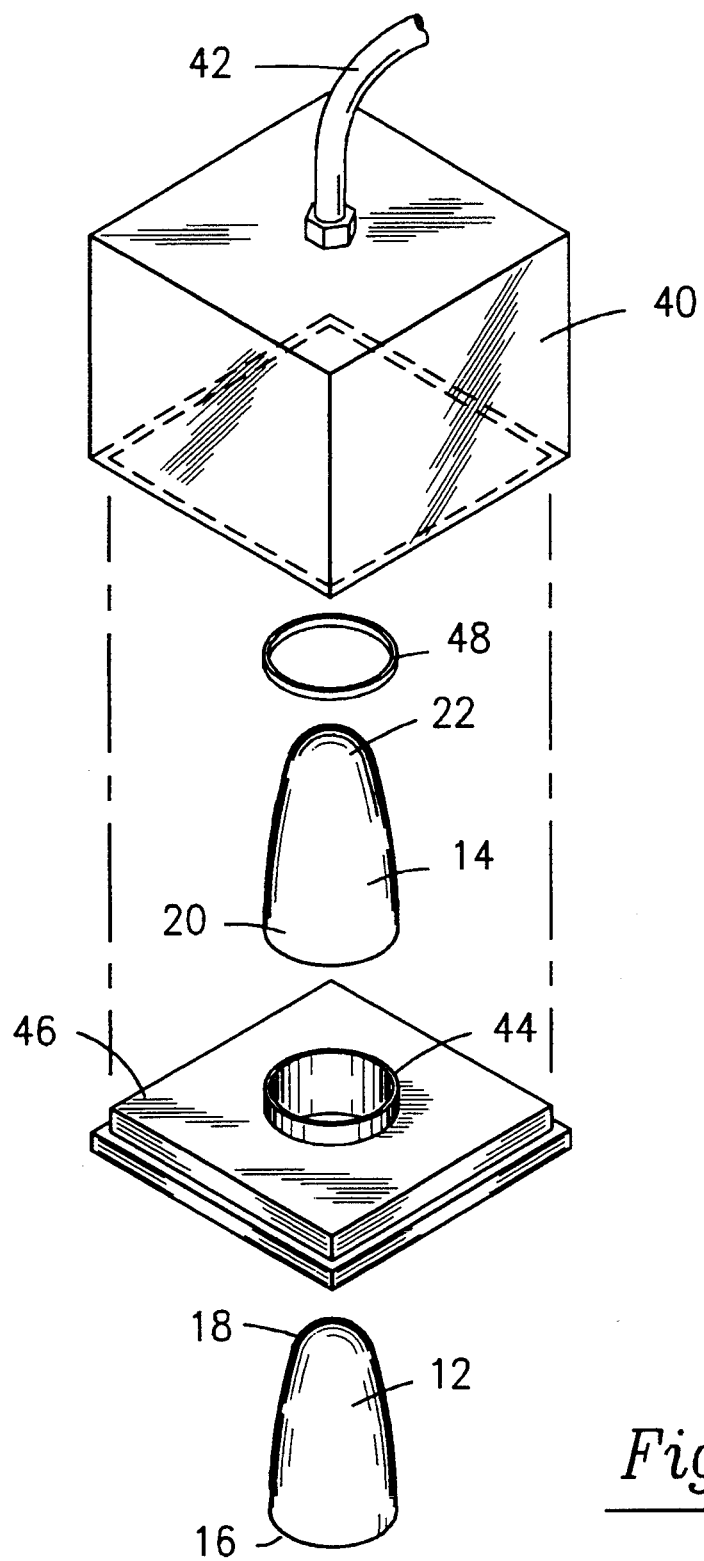
FIG. 7 is an exploded perspective view of the novel liner and an apparatus for facilitating its assembly.

An alternative method of placing the outer liner 14 over the inner liner 12 is depicted in FIGS. 7 and 8. A vacuum chamber 40 is connected to a suitable source of negative pressure, not shown, through a vacuum hose 42. A rim means 44 is positioned in a preselected wall 46 of the chamber 40, and the open proximal end 20 of the outer liner 14 is stretched and placed around said rim as shown in FIG. 8. A retainer ring 48 is positioned around open end 14 to hold it onto rim means 44. The source of negative pressure is then activated, and the resulting loss of pressure in the vacuum chamber 40 causes the outer liner 14 to enlarge as shown in FIG. 8 because the interior thereof remains exposed to atmospheric pressure. While the outer liner is enlarged, the inner liner 12 is placed-thereinto and the source of negative pressure is deactivated so that the outer liner 12 returns to its original shape and size, thereby closing tightly around the inner liner and adhering thereto when the adhesive cures.

The inner liner 12 is rolled onto a base member 13 (FIG. 8) preparatory to its insertion into the outer liner 14 by first rolling it inside out and then returning it to its initial configuration by unrolling it onto said base 13. Base 13 is mounted on a horizontal surface 15 and a passageway 17 admits ambient air at atmospheric pressure into the interior of the outer liner 14 as depicted in FIG. 8.

Figure 2:
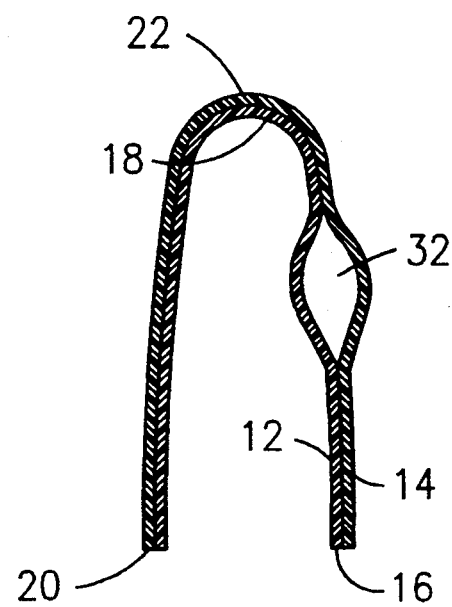
FIG. 2 is a sectional view showing the inner and outer liners in their nested configuration and showing a bladder in an inflated condition.
Figure 3:
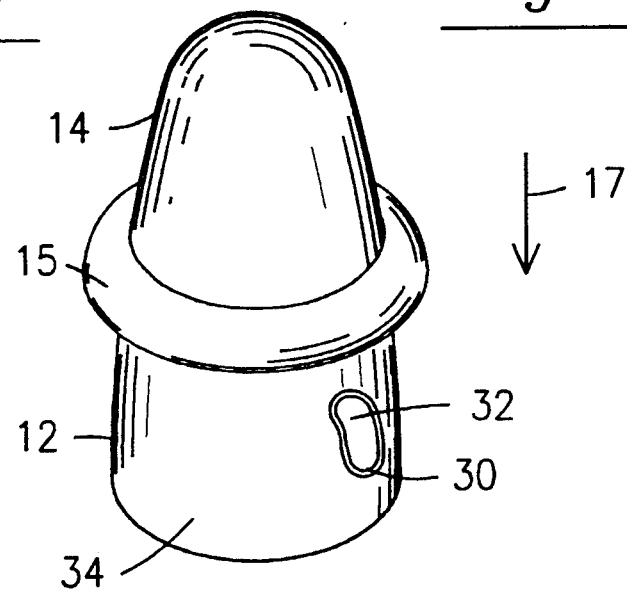
FIG. 3 is a perspective view showing a method for facilitating assembly of the novel liner.

If the inner and outer liners share a common thickness, the bladder 32, when inflated, will deform symmetrically as depicted in FIG. 2. If the thickness of inner liner 12 is less than that of the outer liner, then the bladder will bulge more inwardly than outwardly; conversely, a thinner outer liner will result in an outward bulge greater than its inwardly extending counterpart. An inwardly directed bulge presses against the amputation stump, of course, whereas an outwardly directed bulge bears against the interior of the socket. Whether a symmetrical bulge as depicted in FIG. 2 or a nonsymmetrical bulge is employed is a matter for the discretion of the physician. Similarly, the position, size, shape, and number of bladders 32 is similarly under the control of the prosthetist.

This invention is clearly new and useful. Moreover, it was not obvious to those of ordinary skill in this art at the time it was made, in view of the prior art considered as a whole as required by law.

This invention pioneers the art of customizable yet mass producible liners for prosthetic devices. Accordingly, the claims that follow are entitled to broad interpretation, as a matter of law, to protect from piracy the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings .shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for cushioning the contact between a prosthesis socket and an amputation stump received therewithin, comprising the steps of:

first placing a flexible, elastomeric inner liner in overlying relation to the amputation stump;

next delineating at least one region on said inner liner where a bladder is required;

next circumscribing said delineated region with an application of adhesive that has a narrow width with respect to its extent;

next placing a flexible, elastomeric outer liner into overlying relation to said inner liner so that said adhesive is positioned between said inner and outer liners and bonds them together along the extent of said adhesive when it dries, thereby forming a bladder bounded by said adhesive; and next placing a valve means in fluid communication with said bladder so that air can be selectively added to the bladder and withdrawn therefrom.

2. The method of claim 1, further comprising the steps of rolling said inner liner inside out preparatory to positioning it on said amputation stump and positioning it in overlying relation to said stump by unrolling it thereonto.

3. The method of claim 1, further comprising the steps of rolling said outer liner inside out preparatory to positioning it in overlying relation to said inner liner and positioning it in overlying relation to said inner liner by unrolling it thereonto.

4. The method of claim 1, further comprising the step of injecting a lubricant between said inner and outer liners in preselected areas not adhered to one another to thereby reduce friction between said liners and to reduce friction applied to the patient's skin.

* * * * *